(12) United States Patent
Urano et al.

(10) Patent No.: US 9,310,318 B2
(45) Date of Patent: Apr. 12, 2016

(54) DEFECT INSPECTION METHOD AND DEFECT INSPECTION DEVICE

(71) Applicant: Hitachi High-Technologies Corporation, Minato-ku, Tokyo (JP)

(72) Inventors: Yuta Urano, Tokyo (JP); Toshifumi Honda, Tokyo (JP); Yukihiro Shibata, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/638,305

(22) Filed: Mar. 4, 2015

(65) Prior Publication Data

US 2015/0276623 A1 Oct. 1, 2015

(30) Foreign Application Priority Data

Mar. 25, 2014 (JP) ................................. 2014-062440

(51) Int. Cl.
  *G01J 4/00* (2006.01)
  *G01N 21/956* (2006.01)
  *G01N 21/95* (2006.01)
  *G01N 21/88* (2006.01)

(52) U.S. Cl.
  CPC ........ *G01N 21/956* (2013.01); *G01N 21/95607* (2013.01); *G01N 21/9501* (2013.01); *G01N 2021/8848* (2013.01); *G01N 2021/9513* (2013.01); *G01N 2021/95638* (2013.01)

(58) Field of Classification Search
  CPC .................................. G01J 4/00; G01N 21/21
  USPC .............................................. 356/369, 237.4
  See application file for complete search history.

(56) References Cited

U.S. PATENT DOCUMENTS

| 7,528,942 | B2 * | 5/2009 | Nakano | .................. | G01N 21/47 356/237.1 |
| 2006/0290923 | A1 * | 12/2006 | Nakano | .................. | G01N 21/47 356/237.3 |
| 2012/0194809 | A1 * | 8/2012 | Nakano | .................. | G01N 21/47 356/237.4 |

FOREIGN PATENT DOCUMENTS

JP          2008-39882 A        2/2008

* cited by examiner

*Primary Examiner* — Roy M Punnoose
(74) *Attorney, Agent, or Firm* — Crowell & Moring LLP

(57) ABSTRACT

To detect a bridge defect between lines of a line pattern formed on a sample at pitches narrower than the wavelength of inspection light, a defect inspection device is configured to comprise: a light source which emits laser; a vertical illumination unit which applies the laser to the sample from a vertical direction via an objective lens by converting the laser into linearly polarized light by using a polarization conversion unit in a state polarized in a direction orthogonal to the longitudinal direction of the line pattern; an oblique illumination unit which applies the laser to the sample from an oblique direction; a detection optical unit including an optical filter which selectively transmits a scattered light component from the defect by converting the polarization state of the reflected/scattered light; and a signal processing unit which detects the defect on the sample by processing a detection signal.

10 Claims, 10 Drawing Sheets

F I G. 2 A
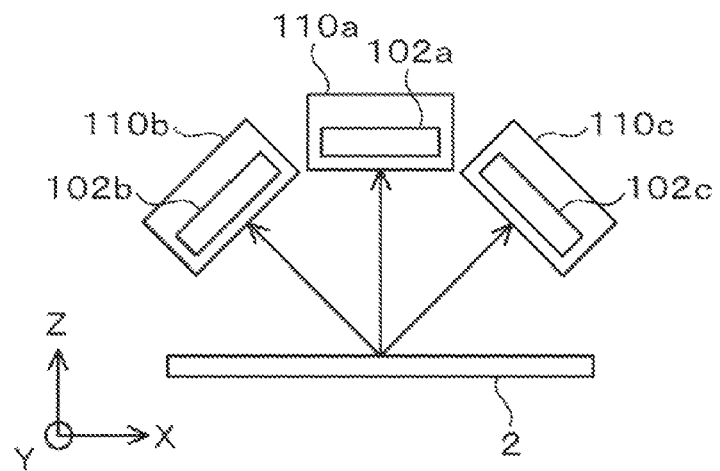
F I G. 2 B
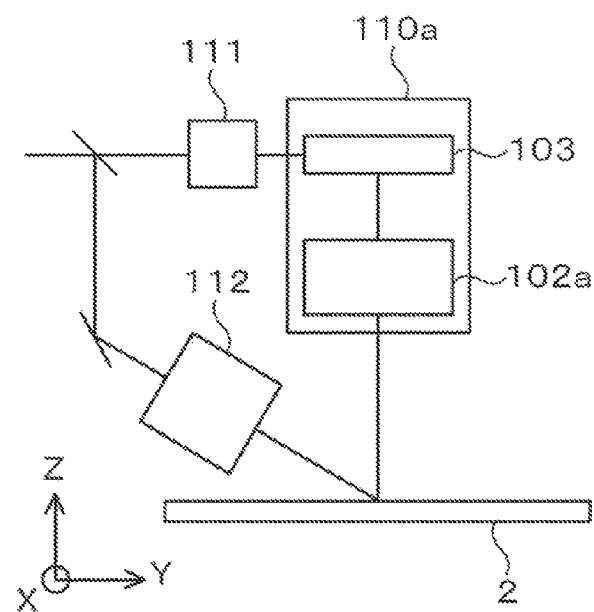

F I G. 2 C
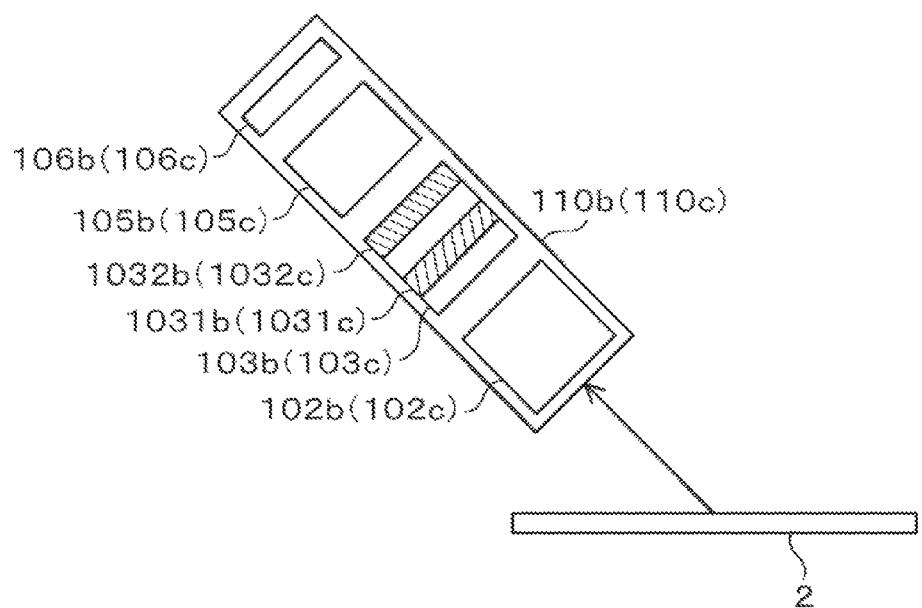
F I G. 3
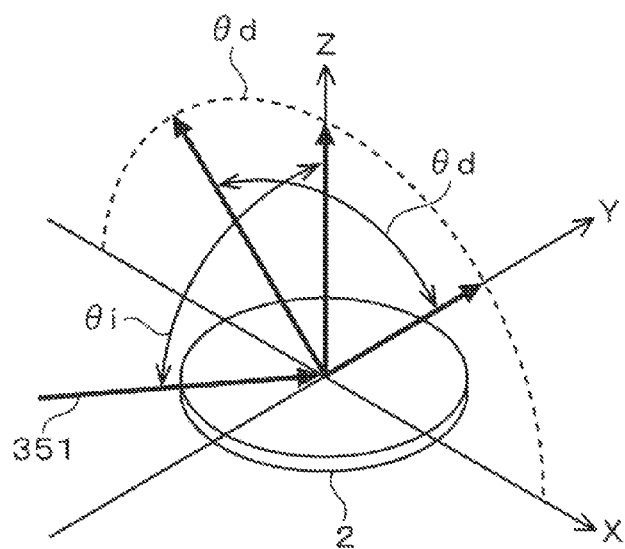

F I G. 1 0 B
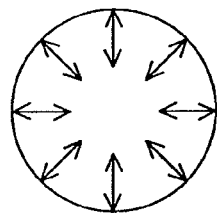
POLARIZATION DISTRIBUTION
OF INCIDENT LIGHT
F I G. 1 0 C
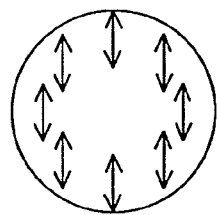
POLARIZATION DISTRIBUTION
OF OUTGOING LIGHT
F I G. 1 1 A
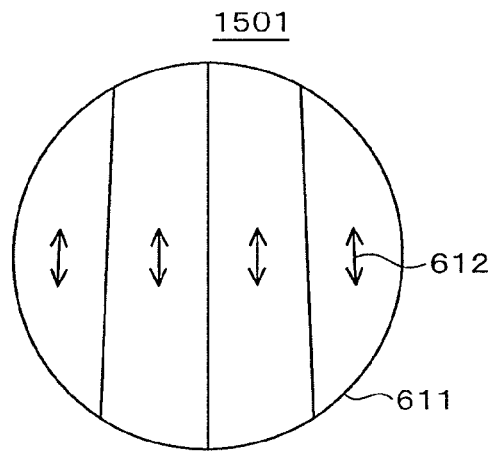

POLARIZATION DISTRIBUTION
OF INCIDENT LIGHT

POLARIZATION DISTRIBUTION
OF OUTGOING LIGHT

DEFECT INSPECTION METHOD AND DEFECT INSPECTION DEVICE

CLAIM OF PRIORITY

The present application claims priority from Japanese Patent Application JP 2014-62440 filed on Mar. 25, 2014, the content of which is hereby incorporated by reference into this application.

BACKGROUND OF THE INVENTION

1. Field of the Invention

The present invention relates to a defect inspection method and a defect inspection device for inspecting the status of occurrence of defects in a manufacturing process for manufacturing a product by forming a pattern on a substrate (semiconductor manufacturing process, liquid crystal display element manufacturing process, printed circuit board manufacturing process, etc.) to be used in a process for detecting the defects, analyzing the occurrence of defects and taking countermeasures against the occurrence of defects.

2. Description of the Related Art

A background technology of this technical field is described in JP-A-2008-39882 (Patent Document 1). In Patent Document 1, light caused by incidence of an optical beam upon a sample or reflected light from the sample is incident upon a polarization control element. The polarization control element causes a phase difference corresponding to the position of the incidence of the light or reflected light upon the polarization control element.

SUMMARY OF THE INVENTION

In optical defect inspection of substrates, it is difficult to detect a bridge defect (also called a "short defect") where parts of a line and space pattern (hereinafter referred to as an "L & S pattern") of a high aspect ratio and a short interval (shorter than or equal to the wavelength of the illuminating light) are locally connected together.

Since the bridge defect exists in a place sandwiched between lines of an L & S pattern having a high aspect ratio and a narrow pitch (short interval), there are cases where having the illuminating light reach the position of the bridge defect is difficult, for example. Further, since the bridge defect has anisotropy in the shape, having the defect cause the scattered light with high efficiency sometimes becomes difficult depending on the correlation between the polarization direction of the illuminating light reaching the defect position and the directional property of the defect. Furthermore, there are also cases where the detection of the scattered light from the defect is difficult due to reflection or absorption of the scattered light from the defect by the L & S pattern around the defect. Moreover, diffracted/scattered light of the illuminating light that is caused by the L & S pattern, roughness of the pattern, disturbance in the periodicity of the pattern, etc. can act as noise and can disable the detection of the scattered light from the defect.

In consideration of the situation described above, the present invention provides a defect inspection device capable of having the aforementioned bridge defect cause scattered light of high intensity sufficient for the detection of the defect. For example, the present invention provides a defect inspection device capable of having the illuminating light reach the position of the bridge defect. The present invention also provides a defect inspection device capable of having a bridge defect in an anisotropic shape cause the scattered light with high efficiency. The present invention also provides a defect inspection device that allows the scattered light from the defect to pass through the L & S pattern around the defect and thereby enables the detection of the scattered light from the defect. The present invention also provides a defect inspection device capable of suppressing the diffracted/scattered light of the illuminating light caused by the L & S pattern, the roughness of the pattern, the disturbance in the periodicity of the pattern, etc. and thereby enabling the detection of the scattered light from the defect. The present invention also provides defect inspection methods achieving the above-described effects.

In accordance with an aspect of the present invention, there is provided a defect inspection device comprising: a light source that emits laser; a vertical illumination unit that applies the laser emitted from the light source to a sample having a line pattern formed thereon from a vertical direction via an objective lens; an oblique illumination unit that applies the laser emitted from the light source to the sample having the line pattern formed thereon from an oblique direction; a detection optical system unit which condenses and detects light that is reflected/scattered from the sample illuminated with the laser applied by the vertical illumination unit or the oblique illumination unit but that enters the objective lens; and a signal processing unit that processes a signal generated by the detection optical system unit to thereby detect a defect on the sample having the line pattern formed thereon. The vertical illumination unit includes a polarization conversion unit that converts the laser emitted from the light source into linearly polarized light, and the vertical illumination unit applies the laser passed through the polarization conversion unit to the line pattern formed on the sample, with the laser being set in a state polarized in a direction orthogonal to a longitudinal direction of the line pattern. And the detection optical system unit includes an optical filter that selectively transmitting a scattered light component from the defect on the sample having the line pattern by converting the polarization state of the reflected/scattered light entered and condensed by the objective lens into linear polarization.

In accordance with another aspect of the present invention, there is provided a defect inspection method comprising the steps of: applying laser emitted from a light source to a sample having a line pattern formed thereon from a vertical direction via an objective lens, or applying laser emitted from the light source to the sample having the line pattern formed thereon from an oblique direction; condensing and detecting light that is reflected/scattered from the sample illuminated with the laser applied from the vertical direction or the oblique direction but that enters the objective lens; and processing a detection signal, thereby detecting a defect on the sample having the line pattern formed thereon. The application of the laser from the vertical direction is performed by first converting the laser emitted from the light source into linearly polarized light, and then applying the linearly polarized laser to the line pattern formed on the sample, with the linearly polarized light being set in a state polarized in a direction orthogonal to a longitudinal direction of the line pattern. The detection is performed by first converting into linear polarization the polarization state of the reflected/scattered light entered and condensed by the objective lens, and then selectively detecting a scattered light component from the defect on the sample having the line pattern.

According to the present invention, a defect inspection device and a defect inspection method capable of inspecting bridge defects (where parts of an L & S pattern of a high aspect ratio and a short interval (shorter than or equal to the wavelength of the illuminating light) are connected together) with high sensitivity can be provided.

These features and advantages of the present invention will be apparent from the following more particular description of preferred embodiments of the invention, as illustrated in the accompanying drawings.

BRIEF DESCRIPTION OF THE DRAWINGS

FIG. 2A is a schematic block diagram of detection optical systems showing the positional relationship among the detection optical systems and an inspection object substrate in the embodiment of the present invention.

FIG. 2B is a schematic block diagram of each illumination section showing the positional relationship between an oblique illumination section and a vertical illumination section in the embodiment of the present invention.

FIG. 2C is a schematic block diagram of oblique detection sections showing the configuration of the oblique detection sections in the embodiment of the present invention.

FIG. 3 is a perspective view of an inspection object substrate showing the relationship among an incident direction of oblique illumination (oblique illuminating light) and detecting directions of detection sections in the embodiment of the present invention.

FIG. 4A is a plan view of an inspection object substrate schematically showing an example of a bridge defect on an L & S pattern formed on the inspection object substrate.

FIG. 4B is a front view of a D-D cross section of the inspection object substrate in FIG. 4A, showing a state in which vertical illumination is given to the bridge defect on the L & S pattern formed on the inspection object substrate.

FIG. 10B is a schematic diagram showing the status of polarization distribution of scattered light from the inspection object substrate entering the polarization conversion element of the vertical detection section in the embodiment of the present invention.

FIG. 10C is a schematic diagram showing the status of polarization distribution of the scattered light from the inspection object substrate after passing through the polarization conversion element of the vertical detection section in the embodiment of the present invention.

FIG. 11A is a plan view showing the configuration of a polarization conversion element of the oblique detection section in the embodiment of the present invention.

DESCRIPTION OF THE PREFERRED EMBODIMENTS

Figure 1A:
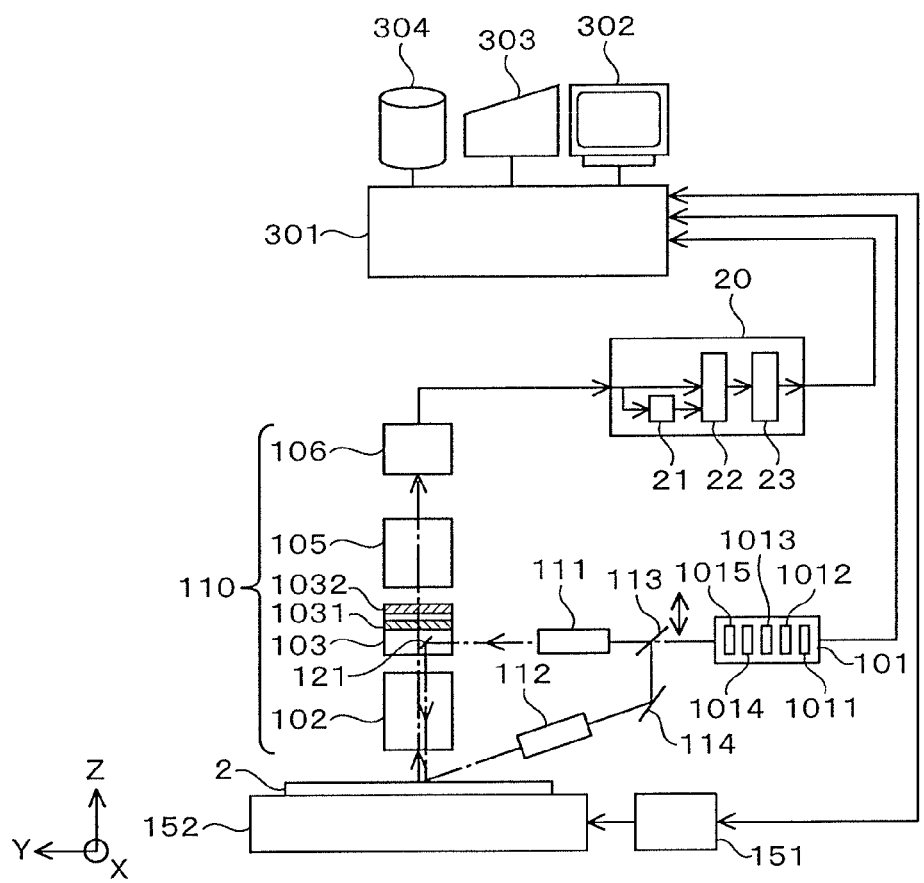
FIG. 1A is a block diagram showing the overall configuration of a defect inspection device in accordance with an embodiment of the present invention.

The present invention relates to a defect inspection method and a defect inspection device for inspecting the status of occurrence of defects in a manufacturing process for manufacturing a product by forming a pattern on a substrate (semiconductor manufacturing process, liquid crystal display element manufacturing process, printed circuit board manufacturing process, etc.) to be used in a process for detecting the defects, analyzing the occurrence of defects and taking countermeasures against the occurrence of defects.

Inspection of a bridge defect (where parts of an L & S pattern of a high aspect ratio and a short interval (shorter than or equal to the wavelength of the illuminating light) are connected together) with high sensitivity is made possible by employing an illumination optical system and a detection optical system having the following features for the defect inspection device: The illumination optical system condenses light into a linear shape that is long in one direction so that the polarization direction of the light after passing through a condensing optical element is in a plane orthogonal to the longitudinal direction of the L & S pattern on the substrate in the entire region within the aperture angle range of the condensing of light, and gives illumination having a component whose polarization direction at the condensing position is orthogonal to the substrate. The detection optical system detects a polarization component of the scattered light (caused by the illumination) that is in a latitude direction of a celestial sphere centering at the field of view of the detection.

Referring now to the drawings, a description will be given in detail of a preferred embodiment of the present invention.

FIG. 1A is a block diagram showing an example of the configuration of a defect inspection device in accordance with an embodiment of the present invention. The defect inspection device according to this embodiment comprises a light source section 101, a vertical illumination section 111, an oblique illumination section 112, a vertical illumination mirror 121, an objective lens 102, a detection optical filter section 103, an imaging lens 105, a detector 106, a processing section 20, an overall control section 301, a display section 302, a computation section 303, a storage section 304, a stage drive section 151, and an X-Y-Z-θ stage 152 (hereinafter referred to simply as a "stage 152").

The outline of the operation of the defect inspection device according to this embodiment will be explained below. Illuminating light is applied to an inspection object substrate 2 from a vertical direction by the light source section 101, the vertical illumination section 111, the vertical illumination mirror 121 and the objective lens 102. Along with or individually from the illumination from the vertical direction, illuminating light is applied to the inspection object substrate 2 from an oblique direction by the light source section 101 and the oblique illumination section 112. Light (reflected light, diffracted light, scattered light) from the inspection object substrate 2 is condensed by the objective lens 102, received by the detector 106 via the detection optical filter section 103 and the imaging lens 105, and converted by the detector 106 into an image signal.

According to the acquired image signal, the processing section 20 makes a defect judgment. The processing section 20 includes an image memory 21, an image comparison section 22 and a defect extraction section 23. In the processing section 20, an output signal from the detector 106 detecting the scattered light from the inspection object substrate 2 is inputted to the image memory 21 and the image comparison section 22 and stored in the image memory 21.

The image comparison section 22 compares image data inputted from the detector 106 with image data previously stored in the image memory 21 (image data acquired by detecting scattered light from a part from which the same image data as the inputted image data should normally be acquired) and calculates the difference between the inputted image data and the previously stored image data. The defect extraction section 23 compares the calculated difference value (between the inputted image data and the previously stored image data) with a preset threshold value and extracts image data having a difference value greater than the threshold value as defect candidates.

Information on the defect candidates extracted by the defect extraction section 23 is stored in the storage section 304 and displayed on the display section 302 via the overall control section 301. The inspection object substrate 2 is scanned by the stage 152 which is driven by the stage drive section 151 and the entire surface of the inspection object substrate 2 is inspected.

The light source section 101 includes a laser light source 1011, an attenuator 1012, an ND filter 1013, a wave plate 1014 and a beam expander 1015. In the light source section 101, illuminating light emitted from the laser light source 1011 successively passes through the attenuator 1012, the ND filter 1013, the wave plate 1014 and the beam expander 1015, by which the light amount, the polarization state, the beam diameter and the shape of the illuminating light are adjusted and controlled. The light source section 101 outputs the illuminating light adjusted and controlled as above. The optical path of the illuminating light emitted from the light source section 101 is switched by positioning a mirror 113 in or out of the optical path, by which the illuminating light is lead to the vertical illumination section 111 or the oblique illumination section 112. A laser light source of a short wavelength, high output power, high luminance and high stability is suitable as the laser light source 1011. For example, a laser light source using the third, fourth or fifth harmonic of a YAG laser can be employed as the laser light source 1011.

While only one detection section 110 (formed of the objective lens 102, the detection optical filter section 103, the imaging lens 105 and the detector 106) is shown in FIG. 1A, two or more detection sections may be arranged at positions where their objective lenses do not mechanically interfere with each other. When the defect inspection device comprises two or more detection sections, the processing section 20 makes the defect judgment by processing detection signals from the two or more detection sections.

In cases where the defect inspection device comprises a single detection section 110 like the example shown in FIG. 1A, a large NA (Numerical Aperture) of the detection section can be secured and high spatial resolution and high detection efficiency can be provided, which is effective for the inspection of minute defects. In cases where the defect inspection device comprises two or more detection sections 110, it is possible to selectively detect scattered light in a particular direction effective for the detection of each defect/pattern in cases where the directional property of the scattered light varies depending on the defect/pattern, which is effective for improvement of capture ratio of the defect signal and reduction of false detection.

FIG. 2A is a schematic diagram showing an example of the positional relationship among objective lenses 102a, 102b and 102c of detection sections 110a, 110b and 110c in a case where the defect inspection device comprises two or more detection sections. FIG. 2B is a schematic diagram showing the positional relationship between the vertical illumination section 111 and the oblique illumination section 112. A plane containing the inspection object substrate 2 is defined as an XY plane. The direction of a normal line to the inspection object substrate 2 will be referred to as a Z direction. The main scan direction and the auxiliary scan direction of the stage will be referred to as an X direction and a Y direction, respectively The objective lenses 102a, 102b and 102c of the three detection sections 110a, 110b and 110c have their optical axes in an XZ plane. The objective lens 102a of a vertical detection section 110a is arranged in the Z direction. The vertical detection section 110a detects light from the inspection object substrate 2 emitted in the Z direction. The objective lenses 102b and 102c of oblique detection sections 110b and 110c are arranged on both sides of the objective lens 102a of the vertical detection section 110a. The oblique detection sections 110b and 110c detect light from the inspection object substrate 2 emitted in directions oblique to the Z direction.

FIG. 2C is a block diagram showing the configuration of the oblique detection sections 110b and 110c. Each of the oblique detection section 110b (having the objective lens 102b) and the oblique detection section 110c (having the objective lens 102c) is configured to include a detection optical filter section (103b, 103c), an imaging lens (105b, 105c) and a detector (106b, 106c) similarly to the detection section 110, which corresponds to the vertical detection section 110a, explained by referring to FIG. 1A. However, the configuration of the oblique detection sections 110b and 110c slightly differs from that of the vertical detection section 110a in that the oblique detection sections 110b and 110c include no mirror 121 shown in FIG. 1A. Since the oblique detection sections 110b and 110c are identical with each other in the configuration, only one of the oblique detection sections is shown in FIG. 2C.

In the configuration shown in FIG. 1A, the illuminating light emitted from the light source section 101 is selectively lead to the vertical illumination section 111 or the oblique illumination section 112 by positioning the mirror 113 in or out of the optical path by use of a vertical drive mechanism (not shown). It is also possible to lead the illuminating light to both the vertical illumination section 111 and the oblique illumination section 112 by splitting the optical path by using a beam splitter instead of the mirror 113.

In the configuration shown in FIG. 1A, when the mirror 113 is placed on standby at a position out of the optical axis of the illuminating light emitted from the light source section 101 by a vertical drive mechanism (not shown), the illuminating light from the light source section 101 enters the vertical illumination section 111. The illuminating light after passing through the vertical illumination section 111 is reflected to a different direction by the vertical illumination mirror 121 arranged at or in the vicinity of the pupil position of the objective lens 102a and is lead to the inspection object substrate 2 via the objective lens 102a. The angle of incidence of the illuminating light upon the sample (inspection object substrate 2) from above can be changed within the extent of the NA of the objective lens 102 by changing the position of the mirror 121 in the Y direction.

Figure 1B:
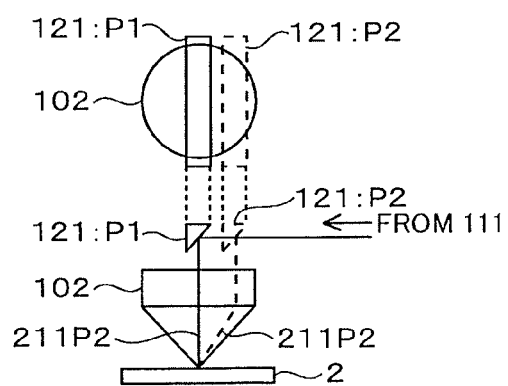
FIG. 1B is a view showing the configuration of a vertical illumination section in the embodiment of the present invention.

FIG. 1B indicates the relationship among the objective lens 102, the vertical illumination mirror 121 and the inspection object substrate 2 shown in FIG. 1A. In FIG. 1B, is a view of the objective lens 102 and the vertical illumination mirror 121. In the configuration shown in FIG. 1B, when the Y-direction position of the vertical illumination mirror 121 is set at P1 coinciding with the optical axis (central axis) of the objective lens 102, the illuminating light after passing through the vertical illumination section 111 is reflected by the vertical illumination mirror 121 placed at the position P1, passes through the objective lens 102, and is applied to the inspection object substrate 2 as incident light 211P1 from a substantially vertical direction.

On the other hand, when the Y-direction position of the vertical illumination mirror 121 is set at P2 deviating from the optical axis (central axis) of the objective lens 102 within the field of view of the objective lens 102, the illuminating light after passing through the vertical illumination section 111 is reflected by the vertical illumination mirror 121 placed at the position P2, passes through the objective lens 102, and is applied to the inspection object substrate 2 as incident light 211P2 from an oblique direction with respect to the central axis.

As above, the incident angle of the illuminating light applied to the inspection object substrate 2 can be changed by moving the position of the vertical illumination mirror 121 within the field of view of the objective lens 102 by using a drive means (not shown). As a result, the detection rate (capture rate) of defects that should be detected can be increased by properly setting the position of the vertical illumination mirror 121 at an optimum position depending on the inspection object and the type of the defect that should be detected. This increases the detection rate (capture rate) of asymmetric defects.

In the configuration shown in FIG. 1A, when the mirror 113 is positioned by a vertical drive mechanism (not shown) on the optical axis of the illuminating light emitted from the light source section 101, the illuminating light from the light source section 101 is reflected by the mirror 113 toward the mirror 114, reflected by the mirror 114, and enters the oblique illumination section 112. The illuminating light after passing through the oblique illumination section 112 travels outside the objective lens 102a and is lead to the inspection object substrate 2 through an optical path in the YZ plane and oblique to the Z-axis direction.

The illuminating light is lead to the inspection object substrate 2 through the optical system (optical path) via the vertical illumination section 111 or through the optical system (optical path) via the oblique illumination section 112, while being condensed by an optical system (explained later) into a linear beam shape (that is long in the Y direction and short in the X direction) on the surface of the inspection object substrate 2. The center of the field of view of each of the objective lenses 102a, 102b and 102c of the detection sections has been adjusted to the condensing position of the illuminating light.

FIG. 3 shows the relationship among the incident direction of the oblique illumination (oblique illuminating light) and detecting directions of the detection sections. The incident angle of the illuminating light 351 for the oblique illumination (light that passed through the oblique illumination section 112) upon the surface of the inspection object substrate 2 will hereinafter be represented as θi. The detection angle of the oblique detection section performing the detection in a direction oblique to a normal line of the inspection object substrate 2 (i.e., oblique detection section having the objective lens 102b or 102c in FIG. 2A) will hereinafter be represented as θd. The two oblique detection sections are arranged in directions symmetrical with each other with respect to the YZ plane (±θd).

FIGS. 4A and 4B are schematic diagrams showing an example of a case where the vertical illumination is applied to a bridge defect on a high-aspect-ratio narrow-pitch L & S pattern. FIG. 4B is a cross-sectional view taken along the line D-D in FIG. 4A. While the longitudinal direction of the line pattern 201 is the Y direction in the illustrated example, the longitudinal direction can also be set in the X direction by changing the direction of setting the inspection object 2. A bridge defect 202 exists between two lines of a high aspect ratio line pattern 201. The height of the bridge defect 202 is generally equivalent to or less than the height of the line pattern 201 as shown in FIG. 4B.

In the direction orthogonal to the longitudinal direction of the L & S pattern (i.e., in the X direction in FIG. 4), the line pattern 201 can be regarded as iteration of an intermittent pattern shorter than or equal to the wavelength of the illuminating light. Therefore, the oscillation of free electrons or polarization does not follow the electric field oscillation in the direction and the L & S pattern exhibits an optical response like that of an insulator. Thus, even when the light absorption rate of the material of the line pattern 201 is high, light whose polarization direction is orthogonal to the longitudinal direction of the L & S pattern tends to pass through the pattern.

In contrast, a polarization component in parallel with the longitudinal direction of the L & S pattern highly interacts with the line pattern 201, undergoes strong reflection/scattering at the line pattern 201, and hardly reaches the inside 203 of the L & S pattern. Therefore, in order to have the illuminating light travel through the L & S pattern (whose pitch (line interval) is shorter than the wavelength) to the inside 203 and reach the bridge defect 202, the use of illuminating light polarized in the direction orthogonal to the longitudinal direction of the L & S pattern (i.e., X direction in FIGS. 4A and 4B) is effective. Incidentally, the "polarization direction" means, in general, the oscillation direction of the electric field of light and the oscillation direction of the magnetic field of light, and in this specification it means the oscillation direction of the electric field.

The vertical illumination satisfies the above condition when the conditions shown in FIG. 4B (incident direction 211: Z direction, polarization direction 212: X direction) are satisfied.

Further, the bridge defect 202 has anisotropy in the shape; the length in the Z direction is greater than the lengths in the X and Y directions. Therefore, in order to generate a strong scattered light from the defect, it is effective to form Z direction polarization (electric field oscillation in Z direction) 216 at the defect position with the illuminating light.

Figure 4C:
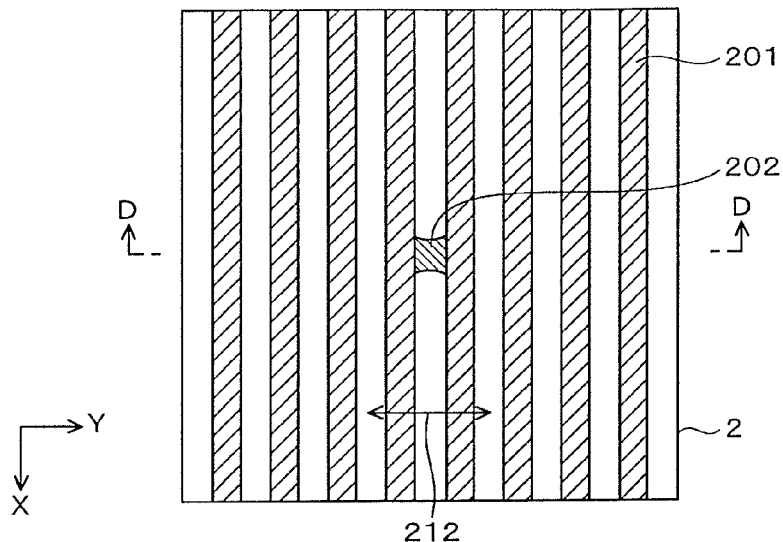
FIG. 4C is a plan view of the inspection object substrate schematically showing the example of the bridge defect on the L & S pattern formed on the inspection object substrate.
Figure 4D:
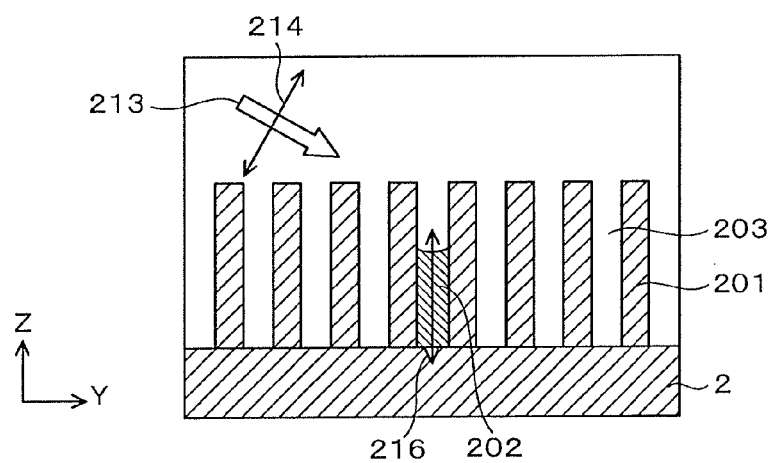
FIG. 4D is a front view of a D-D cross section of the inspection object substrate in FIG. 4C, showing a state in which oblique illumination is given to the bridge defect on the L & S pattern formed on the inspection object substrate.

On the other hand, the oblique illumination satisfies the aforementioned condition when the following conditions shown in FIGS. 4C and 4D are satisfied: the line pattern 201 has been rotated 90 degrees from the state of FIG. 4A, as shown in FIG. 4C; and the incident direction 213 is in parallel with the YZ plane and the polarization direction 214 is in the YZ plane (p-polarization), as shown in FIG. 4D.

Figure 5A:
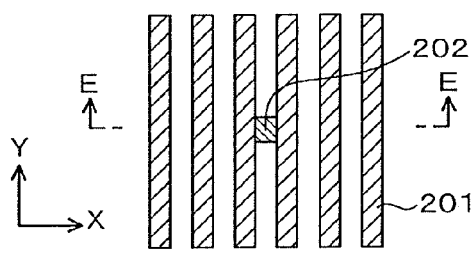
FIG. 5A is a plan view of an inspection object substrate schematically showing an example of a bridge defect on an L & S pattern formed on the inspection object substrate.
Figure 5B:
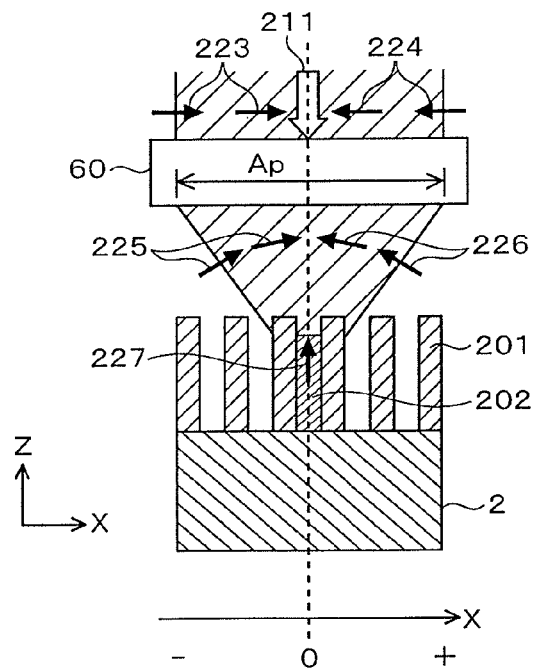
FIG. 5B is a front view of the E-E cross section of the inspection object substrate in FIG. 5A, showing polarization directions of illuminating light in a state in which the vertical illumination is given to the bridge defect on the L & S pattern formed on the inspection object substrate.
Figure 5C:
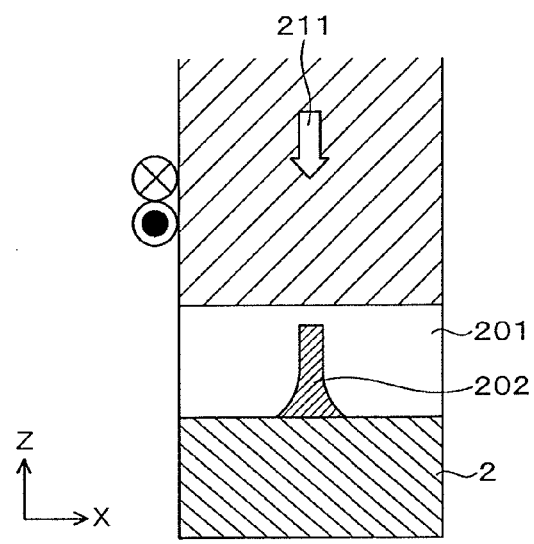
FIG. 5C is a side view of a cross section of the inspection object substrate at the origin O in the X direction in FIG. 5B, showing the polarization directions of the illuminating light in the state in which the vertical illumination is given to the bridge defect on the L & S pattern formed on the inspection object substrate.

FIGS. 5A-5C are schematic diagrams showing the polarization direction of the vertical illumination 211 with respect to the L & S pattern. FIG. 5B is a cross-sectional view taken along the line E-E in FIG. 5A. FIG. 5C is a side view of FIG. 5B, that is, a cross-sectional view taken along the center line in FIG. 5B. By setting the vertical illumination 211 (vertical illuminating light) as linear polarization in the X direction (linearly polarized light polarized in the X direction), the illuminating light travels through the L & S pattern to the inside of the patterns and reaches the defect 202. The illumination (illuminating light) is condensed in the X direction by a vertical illumination condensing section 221 (corresponding to the configuration from the vertical illumination section 111 to the objective lens 102a in FIG. 2B) and forms linear illumination (linear illuminating light) that is short in the X direction and long in the Y direction on the inspection object substrate 2 (see FIG. 5C).

In ordinary type of linear polarization illumination, the sign of the Z component of the amplitude of the illuminating polarized light after passing through the vertical illumination condensing section 221 inverts between the region where X>0 and the region where X<0 in the illumination condensing aperture range. Accordingly, the Z component of the polarized light is canceled out at the condensing position and electric field amplitude in the X direction is formed. In contrast, in this embodiment, a polarization state in which the electric field oscillation direction 223 in the region where X<0 (in the illumination condensing aperture range) and the electric field oscillation direction 224 in the region where X>0 (in the illumination condensing aperture range) are opposite to each other in the X direction (i.e., a state in which the polarization in the region where X<0 and the polarization in the region where X>0 are both linear polarizations in the X direction with a 180-degree phase difference from each other) is formed in the luminous flux before passing through the vertical illumination condensing section 221.

Accordingly, after passing through the vertical illumination condensing section 221, the signs of the Z components coincide with each other and the signs of the X components are opposite to each other (sign inversion) between the oscillation direction 225 in the region where X<0 (in the illumination condensing aperture range Ap) and the oscillation direction 226 in the region where X>0 (in the illumination condensing aperture range Ap). Consequently, the X component of the polarized light is canceled out at the condensing position and electric field amplitude 227 in the Z direction is formed. With the above configuration, it is possible to let the illuminating light reach the position of the defect 202 (defect position) with high efficiency since the polarization of the illumination is orthogonal to the longitudinal direction of the L & S pattern. Further, since the polarization 227 in the Z direction is formed at the defect position, strong scattered light can be obtained from the defect.

Figure 6:
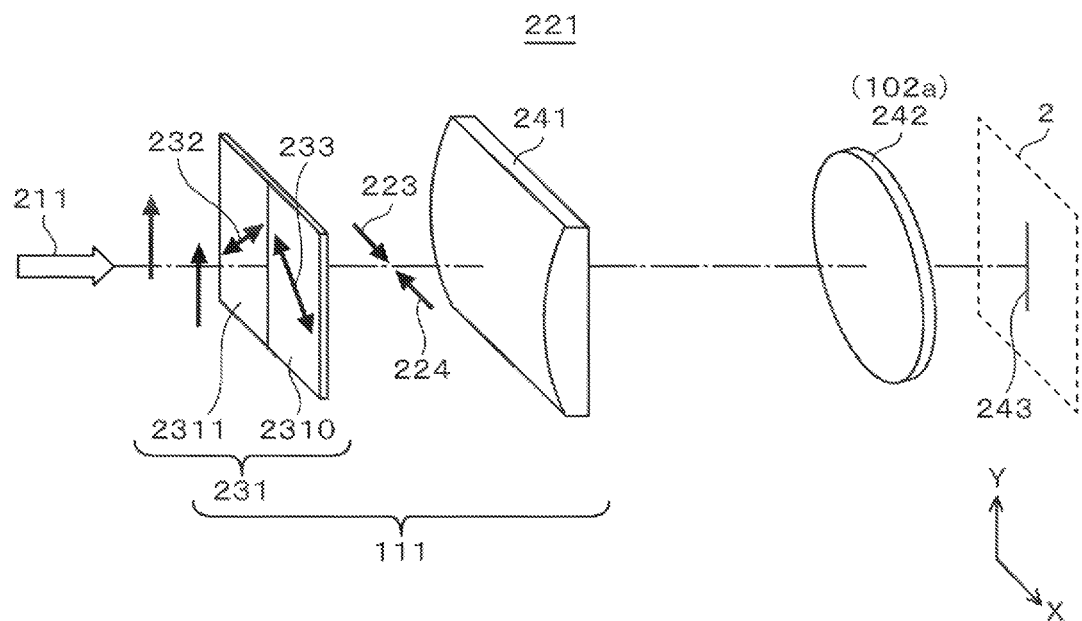
FIG. 6 is a schematic block diagram showing the overall configuration of a vertical illumination optical system in the embodiment of the present invention.

FIG. 6 shows an example of the configuration of the vertical illumination condensing section 221 formed by combining the vertical illumination section 111 and the objective lens 102. The linearly polarized illuminating light emitted from the light source section 101 enters the vertical illumination section 111 and is converted by a two split wave plate 231 into linear polarizations in opposite directions (+X direction 223 and −X direction 224). The X and Y directions in this example correspond to the X and Y directions on the inspection object substrate 2. Thereafter, the illuminating light is condensed by a cylindrical lens 241 and a condensing lens 242 (corresponding to the objective lens 102 in FIG. 1A) into a linear spot 243 that is long in the Y direction on the surface of the inspection object substrate 2.

The two split wave plate 231 has a function of a half-wave plate in which the fast axis (phase advancement axis) in the region where X>0 and the fast axis in the region where X<0 (when the optical axis (center) of the illuminating light is defined as X=0) are orthogonal to each other. The example shown in FIG. 6 has a configuration as a combination of a half-wave plate 2311 whose fast axis 232 is +45 degrees oblique to the Y-axis and a half-wave plate 2312 whose fast axis 233 is −45 degrees oblique to the Y-axis. By inputting linear polarization in the Y direction (linearly polarized light polarized in the Y direction) to the tow split wave plate 231, the polarization is rotated by ±90 degrees and linear polarizations 223 and 224 in opposite directions are obtained. The illuminating light is condensed into a linear shape by the combination of the cylindrical lens 241 and the condensing lens 242. The objective lens 102a of the vertical detection section 110a serves also as the condensing lens 242. With this configuration, it becomes possible to form the linear illumination spot 243 by the one-dimensional condensing of the illuminating light while also acquiring a two-dimensional image by the two-dimensional imaging with the detection optical system (e.g., the detection section 110 shown in FIG. 1A).

A photonic crystal element obtained by forming an anisotropic pattern (with a sub-wavelength pitch (interval) shorter than the wavelength of the transmitted light) on a transparent substrate to give a prescribed birefringent property to each region, or an element obtained by joining two half-wave plates (each of which is made of an anisotropic crystal) together while changing the crystal orientation by 90 degrees can be used as the two split wave plate 231. The former element has the following advantages: Since the pattern is formed on one transparent substrate, high wave front accuracy of the transmitted light can be maintained; Further, since the element is formed by fine processing by means of lithography, ill effect of the gap at the interface between adjoining regions is negligible.

On the other hand, the former element has a disadvantage in that the transmittance drops due to the influence of the scattering by the fine pattern having width of subwavelength. In contrast, the latter element has an advantage in that high transmittance can be achieved by an appropriate antireflection coating. In the latter element, in order to maintain high wave front accuracy of the transmitted light, the substrate surfaces of the two substrates jointed together are required to be in parallel with each other with high accuracy on the order of the wavelength of the transmitted light. This can be implemented by preparing a substrate having guaranteed surface accuracy as a reference surface and pressing the two half-wave plates against the reference surface. The maintenance of high wave front accuracy of the transmitted light is a condition necessary for the condensing the transmitted light from the two split wave plate 231 into a thin linear spot. High wave front accuracy of the transmitted waves within λ/4 (preferably, within λ/10) is at least necessary.

Figure 7:
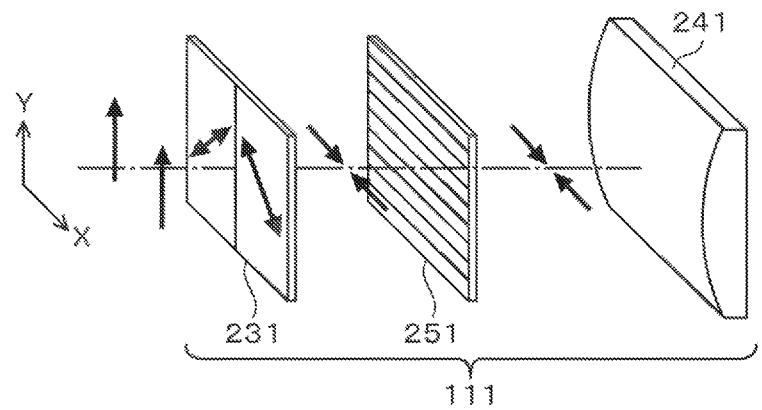
FIG. 7 is a schematic block diagram showing the overall configuration of a modified example of the vertical illumination optical system in the embodiment of the present invention.

FIG. 7 shows a modified example of the configuration of the vertical illumination section 111. In the short wavelength range (ultraviolet, deep ultraviolet) effective for high-sensitivity detection of minute defects, there exists a problem in that forming a wave plate in an accurately adjusted state (in which the phase difference has been adjusted with high accuracy) is difficult in comparison with wave plates for long wavelength ranges. If the phase difference caused by the wave plate deviates from the designed value, the resultant direction of the polarization deviates from the designed direction. If the phase difference caused by each region of the two split wave plate 231 deviates from the designed value of ½ wavelength (180 degrees), the polarization directions after the passage through the two split wave plate 231 deviate from the ±X directions.

By arranging a polarization plate 251 not transmitting the Y-direction polarization component and transmitting the X-direction linear polarization component between the two split wave plate 231 and the cylindrical lens 241 as shown in FIG. 7, it is possible to remove the Y-direction polarization component and obtain the intended polarizations in the ±X directions. By using a two split wave plate 231 that is made by adjusting the phase difference of a wave plate by grinding, cutting the adjusted wave plate into two wave plates and joining the two wave plates together while changing the orientation by 90 degrees, it is guaranteed that deviations of the phase differences of the two regions of the two split wave plate 231 from the designed values are equal to each other. As a result, deviations of the polarization component directions in the two regions from the X direction become equal to each other and equal intensity balance can be achieved between the polarization component in the +X direction and the polarization component in the −X direction after the passage through the polarizer 251.

Further, even when there is an intensity difference between the polarization component in the +X direction and the polarization component in the −X direction after the passage through the polarizer 251, the intensity balance can be equalized while maintaining the polarization directions after the passage through the polarizer 251, by rotating the two split wave plate 231 around the optical axis of the illuminating light or by rotating the orientation of the linear polarization of the illuminating light entering the two split wave plate 231 by using a wave plate included in the vertical illumination section 111.

Figure 8:
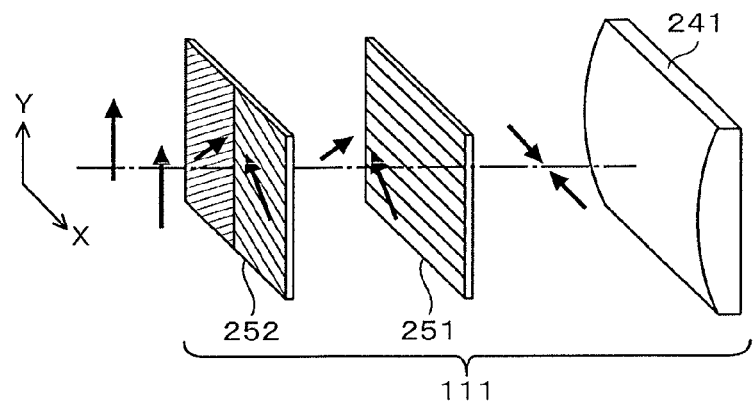
FIG. 8 is a schematic block diagram showing the overall configuration of another modified example of the vertical illumination optical system in the embodiment of the present invention.

FIG. 8 shows another modified example of the configuration of the vertical illumination section 111. In this example, a two split polarization plate 252 is employed in the configuration of FIG. 7 instead of the two split wave plate 231. In FIG. 8, the stripes drawn on the surfaces of the two split polarization plate 252 and the polarization plate 251 indicate the transmission axes of the polarization plates. When illuminating light linearly polarized in the Y direction passes through the two split polarization plate 252, the polarization state of the illuminating light turns into −45-degree linear polarization in the region where X>0 and +45-degree linear polarization in the region where X<0. When the illuminating light further passes through the polarization plate 251, the polarization states turn into linear polarization in the −X direction and linear polarization in the +X direction, respectively.

The two split polarization plate 252 is implemented by a photonic crystal or two polarization plates joined together. Although the achieved illumination intensity decreases to ¼ compared to the configurations shown in FIGS. 6 and 7, this example has an advantage in that there occurs no deviation of the output polarizations from the ±X directions due to the phase difference error of a wave plate, or no intensity difference between the polarization component in the +X direction and the polarization component in the −X direction.

In the oblique illumination performed by the oblique illumination section 112 to make the illuminating light be incident upon the inspection object substrate 2 through a path in the Y-Z plane and oblique to the Z-axis, the inspection object substrate 2 is set so that the longitudinal direction of the L & S pattern is in the X direction and the illuminating light is polarized in the p-polarization. With this setting, illumination polarized in a direction orthogonal to the longitudinal direction of the L & S pattern is formed, which is effective for the inspection of defects inside the L & S pattern. The configuration of the oblique illumination section 112 is substantially equivalent to that of the vertical illumination section 111 which has been explained referring to FIGS. 6-8, and thus repeated explanation thereof is omitted for brevity.

Figure 9:
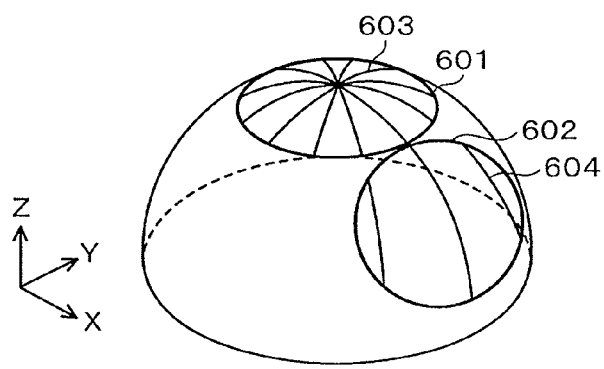
FIG. 9 is a schematic diagram showing the distribution of the polarization direction of scattered light from a bridge defect of an L & S pattern in the embodiment of the present invention.

FIG. 9 shows an example of the distribution of the polarization direction of the scattered light from a bridge defect of the L & S pattern on a celestial spherical surface. By the oblique illumination performed by the oblique illumination section 112 which has been explained referring to FIGS. 1A, 2B and 4B, illuminating light having the polarization component 216 in the Z direction (see FIG. 4B) is applied to the bridge defect 202 which is long in the Z direction so as to cause strong scattered light from the bridge defect 202. If the outgoing direction of the scattered light is represented by associating it with a position on a hemisphere centering at the bridge defect 202 as shown in FIG. 9, the polarization direction of the scattered light caused by the electric field oscillation of the polarization component 216 in the Z direction is represented by a direction parallel to a longitude line of the hemisphere.

In FIG. 9, the polarization direction 603 of the scattered light in the aperture 601 (corresponding to "Ap" in FIG. 5B) of the vertical detection section 110a and the polarization direction 604 in the aperture 602 of the oblique detection section 110b or 110c are shown. By using a polarization filter that transmits polarization components of the scattered light from the defect shown in FIG. 9 in the detection optical filter section of the vertical detection section 110a and the oblique detection section 110b or 110c, it is possible to block irrelevant scattered light (other than the scattered light from the defect) with high light blocking ratio, transmit the scattered light from the defect with high transmittance, and thereby detect the defect with high sensitivity.

In the detection optical filter section 103 of the vertical detection section 110a, a polarization filter that transmits radial polarization distribution is effective since the polarization of the scattered light from the defect is distributed radially on the detection aperture 601. An example of such a polarization filter is a segmented polarization plate which is designed to transmit the radial polarization distribution by using a photonic crystal. Another example of such a polarization filter is a combination of an axisymmetric polarization conversion element and a linear polarizer, which is capable of converting the radial polarization distribution into linearly polarized light and exclusively transmitting the linearly polarized light.

Figure 10A:
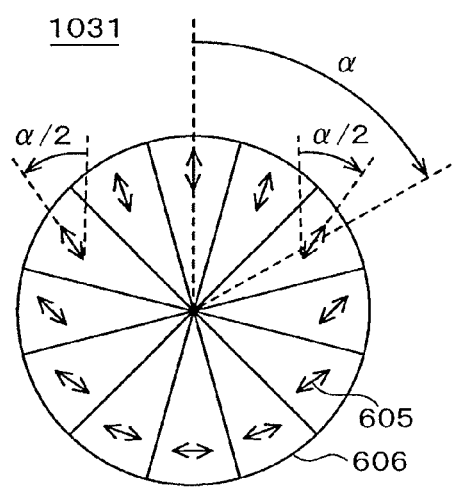
FIG. 10A is a plan view showing the configuration of a polarization conversion element of a vertical detection section in the embodiment of the present invention.

FIG. 10A shows an example of such an axisymmetric polarization conversion element 1031. The axisymmetric polarization conversion element 1031 is formed of a plurality of half-wave plates arranged so that the direction of the fast axis varies depending on the in-plane orientation. Each arrow 605 in FIG. 10A indicates the direction of the fast axis. The axisymmetric polarization conversion element 1031 is configured so that the fast axis direction in a region at an angle α from a prescribed orientation equals α/2 or −α/2.

By applying such an axisymmetric polarization conversion element 1031 to incident light having a radial polarization distribution 1041 like the one shown in FIG. 10B while placing the center of the element 1031 at the center of the optical axis of the vertical detection section 110a, the radial polarization distribution 1041 of the incident scattered light from the defect is converted into linear polarization 1042 as shown in FIG. 10C (linear polarization in the vertical direction in the case of the fast axis directions shown in FIG. 10A) and outputted from the axisymmetric polarization conversion element 1031. The scattered light from the defect which has been converted into the linear polarization 1042 by the axisymmetric polarization conversion element 1031 is inputted to a linear polarizer 1032. With this configuration, only polarized light deriving from the scattered light from the defect can be selectively transmitted by the linear polarizer 1032 and detected by the detector 106.

Consequently, defect detection with high sensitivity becomes possible. Similarly to the two split wave plate 231, the axisymmetric polarization conversion element 1031 is implemented by a photonic crystal element or an element obtained by joining half-wave plates 606 (each of which is made of an anisotropic crystal) together. To secure necessary imaging performance of the vertical detection section 110a, an element whose transmitted wave front accuracy is at least λ/4 or higher (preferably, λ/10 or higher) is used as the axisymmetric polarization conversion element 1031.

In the detection optical filter sections 103b and 103c of the oblique detection sections 110b and 110c, the polarizations 604 of the scattered light from the defect have a polarization distribution in which the inclination gradually changes in the longitude direction on the detection aperture 602, and thus the use of a polarization filter transmitting such a polarization distribution is effective. FIG. 11A shows an example of a polarization conversion element 1501 which is used for the detection optical filter sections 103b and 103c of the oblique detection sections 110b and 110c. The polarization conversion element 1501 is formed of a combination of half-wave plates 611 (similarly to the axisymmetric polarization conversion element 1031 shown in FIG. 10A) with a different in-plane distribution of the wave plate orientation. The polarization conversion element 1501 for the oblique detection sections 110b and 110c is formed of a plurality of half-wave plates 611 arranged so that the direction 612 of the fast axis varies depending on the in-plane orientation. Each arrow 612 in FIG. 11A indicates the direction of the fast axis.

Figure 11B:
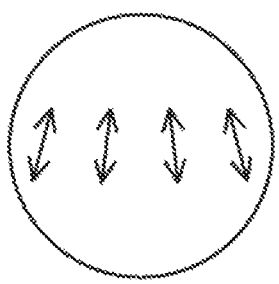
FIG. 11B is a schematic diagram showing the status of polarization distribution of scattered light from the inspection object substrate entering the polarization conversion element of the oblique detection section in the embodiment of the present invention.
Figure 11C:
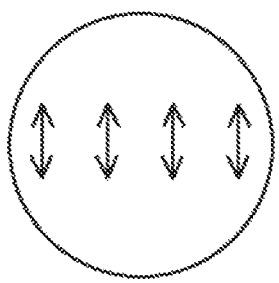
FIG. 11C is a schematic diagram showing the status of polarization distribution of the scattered light from the inspection object substrate after passing through the polarization conversion element of the oblique detection section in the embodiment of the present invention.

The scattered light from the defect on the inspection object substrate 2 enters the polarization conversion element 1501 while having a polarization distribution in directions of longitude lines 604 in the aperture 602 shown in FIG. 9, that is, a polarization distribution indicated by the arrows in FIG. 11B. The polarization conversion element 1501 is formed to have an orientation distribution of the half-wave plates 611 capable of aligning (converting) the polarization distribution of the incident light into a distribution aligned in one direction (as shown in FIG. 11C) in the outgoing light from the polarization conversion element 1501.

Figure 12:
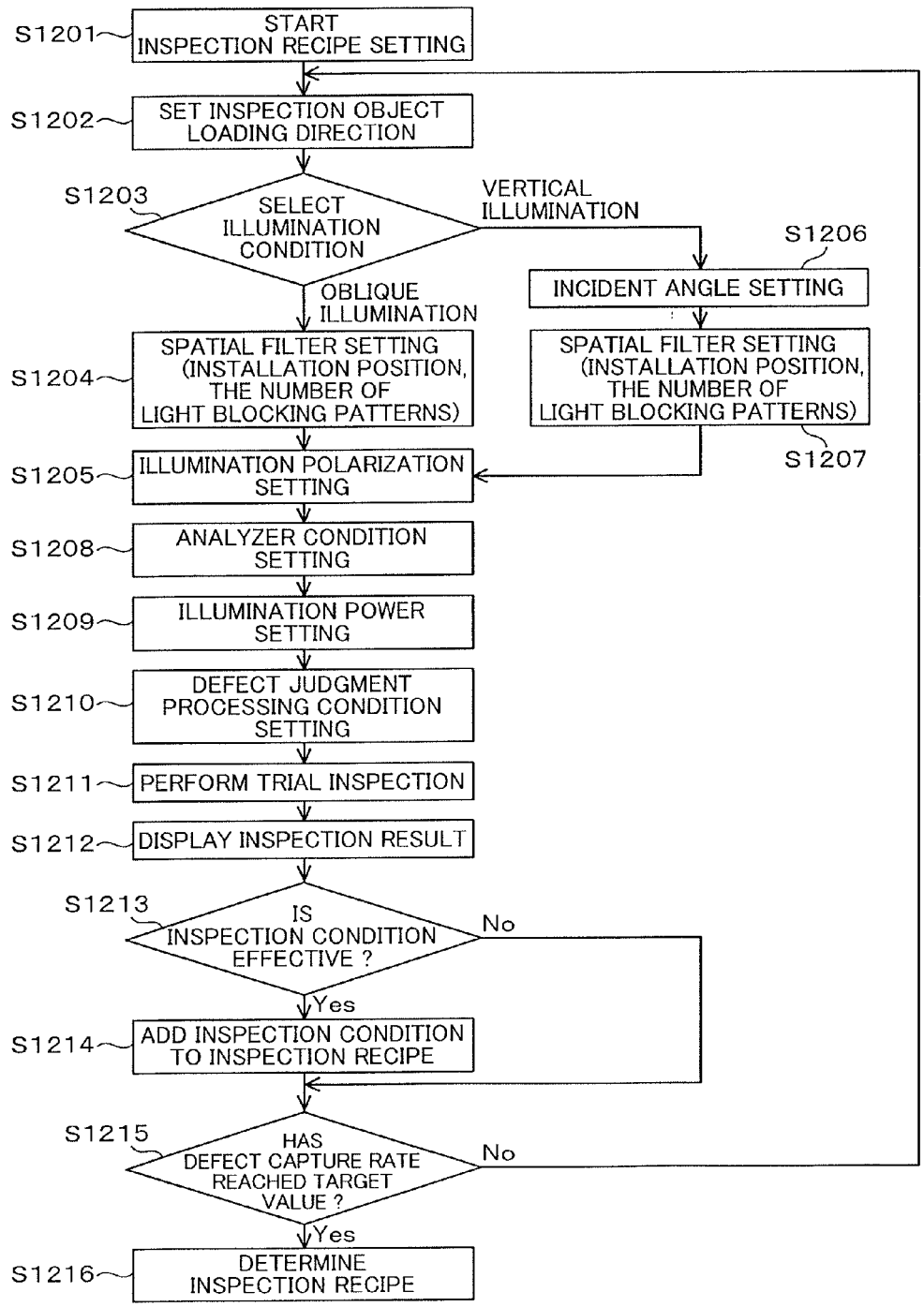
FIG. 12 is a flow chart showing the flow of a process for determining an inspection recipe in the embodiment of the present invention.

FIG. 12 is a flow chart showing an example of a method for setting an inspection recipe in a defect inspection method for setting the inspection recipe and performing the defect inspection according to the inspection recipe. Here, the "inspection recipe" means an inspection condition (illumination condition, detection condition, defect judgment processing condition, etc.) for the inspection or a combination of two or more inspection conditions. In an inspection according to a combination of two or more inspection conditions, inspections under respective inspection conditions are performed successively and the final inspection result is obtained by integrating the results of the inspections under the respective inspection conditions.

To set the inspection recipe, the inspection recipe setting is started (S1201) and a loading direction of the inspection object substrate is set (S1202). The "loading direction" means the orientation of the inspection object where the inspection object substrate is loaded on the stage 152. Subsequently, the illumination condition (vertical illumination or oblique illumination) is selected (S1203). When the oblique illumination is selected, a spatial filter setting is made (S1204), in which the installation position of a spatial filter and the number of light blocking patterns forming the spatial filter are set. Thereafter, the process advances to an illumination polarization setting (S1205) for setting an illumination polarization state. On the other hand, when the vertical illumination is selected in the illumination condition selection (S1203), the incident angle of the vertical illumination (the Y-direction position of the vertical illumination mirror 121 in FIG. 1B) is set (S1206) and then the installation position of a spatial filter and the number of light blocking patterns forming the spatial filter are set (S1207). Thereafter, the process advances to the illumination polarization setting (S1205).

After setting the polarization illumination in the step S1205, an analyzer condition (polarization condition) of each detection section is set (S1208), the analyzer condition setting (S1208) being according to the condition of the analyzer direction (polarization direction) implemented by the polarizer of each detection section. Subsequently, the illumination power is set (S1209) and thereafter the defect judgment processing condition setting is made (S1210) for performing the defect judgment processing. By the above sequence, one inspection condition is determined.

At this point, a trial inspection of the inspection object substrate 2 is performed (S1211) and the inspection result is displayed on the display section 302 (S1212). The inspection result includes the number of detected defects, whether each defect included in a set of defects previously specified as inspection object defects was detected or not, the capture rate, the number of false alarms, a false alarm rate, the number of defects newly detected by using the inspection condition newly set in comparison with a previously set inspection recipe, etc. Based on these items of information, the user judges the effectiveness of the inspection condition (S1213). If the inspection condition is judged to be effective (S1213: YES), the inspection condition is added to the inspection recipe (S1214). Subsequently, a judgment is made on whether the detection capture rate (or the number of detected inspection object defects) achieved by the inspection recipe updated by the above sequence has reached a target value or not (S1215). If the detection capture rate has reached the target value (S1215: YES), the inspection recipe is determined (S1216) and the inspection recipe setting is ended.

If the inspection condition is judged to be not effective in the inspection condition effectiveness judgment step S1213

(S1213: NO), the process advances to the step for judging whether the detection capture rate has reached the target value or not (S1215) without adding the inspection condition to the inspection recipe. If the detection capture rate is judged to have not reached the target value in the judgment step S1215 (S1215: YES), the process returns to the step S1202 and the setting of a new inspection condition is made again.

It is to be noted that the present invention is not limited to the aforementioned embodiments, but covers various modifications. While, for illustrative purposes, those embodiments have been described specifically, the present invention is not necessarily limited to the specific forms disclosed. Thus, partial replacement is possible between the components of a certain embodiment and the components of another. Likewise, certain components can be added to or removed from the embodiments disclosed.

Further note that the control lines and information lines shown above represent only those lines necessary to illustrate the present invention, not necessarily representing all the lines required in terms of products. Thus, it can be assumed that almost all the components are in fact interconnected.

The invention may be embodied in other specific forms without departing from the spirit or essential characteristics thereof. The present embodiment is therefore to be considered in all respects as illustrative and not restrictive, the scope of the invention being indicated by the appended claims, rather then by the foregoing description, and all changes which come within the meaning and range of equivalency of the claims are therefore intended to be embraced therein.

What is claimed is:

1. A defect inspection device comprising:
   a light source that emits laser;
   a vertical illumination unit that applies the laser emitted from the light source to a sample having a line pattern formed thereon from a vertical direction via an objective lens;
   an oblique illumination unit that applies the laser emitted from the light source to the sample having the line pattern formed thereon from an oblique direction;
   a detection optical system unit which condenses and detects light that is reflected/scattered from the sample illuminated with the laser applied by the vertical illumination unit or the oblique illumination unit but that enters the objective lens; and
   a signal processing unit that processes a signal generated by the detection optical system unit to thereby detect a defect on the sample having the line pattern formed thereon,
   wherein, the vertical illumination unit includes a polarization conversion unit that converts the laser emitted from the light source into linearly polarized light and the vertical illumination unit applies the laser passed through the polarization conversion unit to the line pattern formed on the sample, with the laser being set in a state polarized in a direction orthogonal to a longitudinal direction of the line pattern; and
   wherein, the detection optical, system unit includes an optical filter that selectively transmits a scattered light component from the defect on the sample having the line pattern by converting the polarization state of the reflected/scattered light entered and condensed by the objective lens into linear polarization.

2. The defect inspection device according to claim 1, wherein the vertical illumination unit condenses the laser emitted from the light source into a linear shape that is long in one direction, adjusts a longitudinal direction of the condensed laser to the longitudinal direction of the line pattern formed on the sample, and applies the laser to the line pattern formed on the sample, the laser being condensed in the linear shape long in one direction and in the state polarized in the direction orthogonal to the longitudinal direction of the line pattern.

3. The defect inspection device according to claim 1, wherein the oblique illumination unit condenses the laser emitted from the light source into a linear shape that is long in one direction, sets the polarization state of the laser to p-polarization, and applies the laser to the sample having the line pattern formed thereon.

4. The defect inspection device according to claim 1, wherein each of the vertical illumination unit and the oblique illumination unit includes:
   a polarization separation unit that separates the laser emitted from the light source into two beams of polarized light in opposite polarization directions; and
   a lens unit that condenses the two beams of polarized light in opposite polarization directions separated by the polarization separation unit into a linear shape.

5. The defect inspection device according to claim 1, further comprising an oblique detection optical system unit that condenses and detects reflected/scattered light that was reflected/scattered in an oblique direction outside the objective lens of the detection optical system unit, the reflected/scattered light having been reflected/scattered from the sample illuminated with the laser applied by the vertical illumination unit or the oblique illumination unit.

6. A defect inspection method comprising the steps of:
   applying laser emitted from a light source to a sample having a line pattern formed thereon from a vertical direction via an objective lens, or applying laser emitted from the light source to the sample having the line pattern formed thereon from an oblique direction;
   condensing and detecting light that is reflected/scattered from the sample illuminated with the laser applied from the vertical direction or the oblique direction but that enters the objective lens; and
   processing a detection signal, thereby detecting a defect on the sample having the line pattern formed thereon,
   wherein, the application of the laser from the vertical direction is performed by first converting the laser emitted from the light source into linearly polarized light, and then applying the linearly polarized laser to the line pattern formed on the sample, with the linearly polarized light being set in a state polarized in a direction orthogonal to a longitudinal direction of the line pattern; and
   wherein, the detection is performed by first converting into linear polarization the polarization state of the reflected/scattered light entered and condensed by the objective lens, and then selectively detecting a scattered light component from the defect on the sample having the line pattern.

7. The defect inspection method according to claim 6, wherein the application of the laser from the vertical direction is performed by first condensing the laser emitted from the light source into a linear shape that is long in one direction, next adjusting a longitudinal direction of the condensed laser to the longitudinal direction of the line pattern formed on the sample, and then applying the laser to the line pattern formed on the sample, the laser being condensed in the linear shape long in one direction and in the state polarized in the direction orthogonal to the longitudinal direction of the line pattern.

8. The defect inspection method according to claim 6, wherein the application of the laser from the oblique direction is performed by first condensing the laser emitted from the light source into a linear shape that is long in one direction, next setting the polarization state of the laser to p-polarization, and then applying the laser to the sample having the line pattern formed thereon.

9. The defect inspection method according to claim 6, wherein each of the application of the laser from the vertical direction and the application of the laser from the oblique direction is performed by first separating the Laser emitted from the light source into two beams of polarized light in opposite polarization directions, and then condensing the two separated beams of polarized light in opposite polarization directions into a linear shape by using a lens.

10. The defect inspection method according to claim 6, wherein reflected/scattered light in an oblique direction outside the objective lens is condensed and detected, the reflected/scattered light having being reflected/scattered from the sample illuminated with the laser applied from the vertical direction or the oblique direction.

* * * * *